(12) United States Patent
Koike et al.

(10) Patent No.: US 11,640,664 B2
(45) Date of Patent: May 2, 2023

(54) CULTURING ASSISTANCE DEVICE, OBSERVATION DEVICE AND PROGRAM

(71) Applicant: NIKON CORPORATION, Tokyo (JP)

(72) Inventors: Tetsuya Koike, Yamato (JP); Satoshi Takahashi, Yokohama (JP); Yasujiro Kiyota, Tokyo (JP); Shunji Watanabe, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 25 days.

(21) Appl. No.: 16/519,560

(22) Filed: Jul. 23, 2019

(65) Prior Publication Data

US 2019/0347798 A1    Nov. 14, 2019

Related U.S. Application Data

(63) Continuation of application No. PCT/JP2017/040066, filed on Nov. 7, 2017.

(30) Foreign Application Priority Data

Jan. 31, 2017  (JP) .............................. JP2017-015376

(51) Int. Cl.
*G06T 7/00*   (2017.01)
*C12M 1/12*   (2006.01)
(Continued)

(52) U.S. Cl.
CPC ............ *G06T 7/0014* (2013.01); *C12M 37/00* (2013.01); *C12M 41/46* (2013.01); *C12M 41/48* (2013.01);
(Continued)

(58) Field of Classification Search
CPC ....... C12M 37/00; C12M 41/36; C12M 41/46; C12M 41/48; G06T 2200/24;
(Continued)

(56) References Cited

U.S. PATENT DOCUMENTS 7,816,128 B2 * 10/2010 Nakashima ............ C12M 41/48
435/286.2
7,883,887 B2 *  2/2011 Takagi ...................... A61L 2/07
422/26
(Continued)

FOREIGN PATENT DOCUMENTS

EP           1650291 A1 *  4/2006  ............... A61L 2/07
EP         1 944 358 A1    7/2008
(Continued)

OTHER PUBLICATIONS

Office Action, dated Jun. 7, 2022, in Japanese Patent Application No. 2018-565941 (6 pp.).
(Continued)

*Primary Examiner* — Tsung Yin Tsai (57) ABSTRACT

A culturing assistance device includes an image acquisition unit configured to acquire a captured image of cells during culturing at determined times, a storage control unit configured to store the captured image acquired by the image acquisition unit and event information indicating an event related to culturing of the cells, and a learning unit configured to learn a relationship between the stored captured image and the stored event information.

18 Claims, 9 Drawing Sheets

(51) Int. Cl.
*C12M 1/34* (2006.01)
*C12M 1/36* (2006.01)

(52) U.S. Cl.
CPC ............ *G06T 2200/24* (2013.01); *G06T 2207/20081* (2013.01); *G06T 2207/30024* (2013.01)

(58) Field of Classification Search
CPC . G06T 2207/20081; G06T 2207/30024; G06T 7/0014
See application file for complete search history.

(56) References Cited

U.S. PATENT DOCUMENTS

| | | | | |
|---|---|---|---|---|
| 8,478,008 B2* | 7/2013 | Kiyota | ............ | C12M 41/48 382/128 |
| 8,588,504 B2* | 11/2013 | Yano | ............ | C12M 41/14 382/172 |
| 8,902,306 B2* | 12/2014 | Mimura | ............ | C12M 41/36 382/133 |
| 9,296,982 B2* | 3/2016 | Kiyota | ............ | C12M 41/48 |
| 9,567,560 B2* | 2/2017 | Honda | ............ | C12M 41/36 |
| 10,047,335 B2* | 8/2018 | Kiyota | ............ | C12M 23/50 |
| 2004/0029213 A1* | 2/2004 | Callahan | ............ | G06V 20/695 382/128 |
| 2006/0115889 A1* | 6/2006 | Nakashima | ............ | C12M 23/50 435/286.2 |
| 2006/0151185 A1* | 7/2006 | Takagi | ............ | C12M 41/48 172/4 |
| 2011/0228069 A1* | 9/2011 | Mimura | ............ | G02B 21/0088 382/133 |
| 2012/0092478 A1* | 4/2012 | Honda | ............ | C12M 41/46 382/133 |
| 2013/0156287 A1* | 6/2013 | Houjou | ............ | G01N 21/01 382/133 |
| 2015/0087240 A1* | 3/2015 | Loewke | ............ | G06T 7/143 455/67.11 |
| 2017/0199171 A1 | 7/2017 | Kiyota et al. | | |
| 2018/0081180 A1* | 3/2018 | Amino | ............ | G06F 3/0304 |
| 2019/0286908 A1* | 9/2019 | Shintani | ............ | G06V 20/10 |

FOREIGN PATENT DOCUMENTS

| | | | | |
|---|---|---|---|---|
| EP | 1944358 A1 * | 7/2008 | ......... | C12M 23/14 |
| EP | 2 256 212 A1 | 12/2010 | | |
| EP | 2256212 A1 * | 12/2010 | ......... | C12M 23/48 |
| EP | 3 156 477 A1 | 4/2017 | | |
| EP | 3156477 A1 * | 4/2017 | ......... | C12M 41/36 |
| EP | 3 578 633 A1 | 12/2019 | | |
| JP | 3-259078 | 11/1991 | | |
| JP | 2004-229619 | 8/2004 | | |
| JP | 2007-6852 | 1/2007 | | |
| JP | 2012-194691 | 10/2012 | | |
| JP | 2014018186 A * | 2/2014 | ......... | G01N 33/5005 |
| JP | 2016-143354 | 8/2016 | | |
| JP | 2018-528766 | 10/2018 | | |
| WO | WO 2015/193951 A1 | 12/2015 | | |
| WO | WO-2015193951 A1 * | 12/2015 | ......... | C12M 41/36 |
| WO | WO2017/027380 | 2/2017 | | |

OTHER PUBLICATIONS

Extended European Search Report dated Aug. 4, 2020 in corresponding European Patent Application No. 17895201.6.
Ryuji Kato et al., "Cell quality evaluation method using cell image informatics", Seibutsu-Kogaku Kaishi, vol. 88, No. 12, 2010, pp. 646-648.
"Ministry of Economy, Trade and Industry; Japan Agency for Medical Research and Development", Guidelines for design of the human cell culture system (revision), R&D guidelines 2015 (Guidance), Dec. 2015.
International Search Report dated Dec. 12, 2017 in corresponding International Patent Application No. PCT/JP2017/040066.
Written Opinion of the International Searching Authority dated Dec. 12, 2017 in corresponding International Patent Application No. PCT/JP2017/040066.
Notice of Reasons for Refusal, dated Dec. 7, 2021, in Japanese Patent Application No. 2018-565941 (32 pp.).

* cited by examiner

| EVENT (HIERARCHY 1) | EVENT (HIERARCHY 2) | EVENT (HIERARCHY 3) |
|---|---|---|
| EXCHANGE OF CULTURE MEDIUM | IMMEDIATE EXECUTION | ALL EXCHANGE |
| | | HALF AMOUNT EXCHANGE |
| | | . . . |
| | EXECUTION AFTER PREDETERMINED TIME | AFTER THREE HOURS |
| | | AFTER SIX HOURS |
| | | AFTER 24 HOURS |
| | | . . . |
| SUBCULTURING | IMMEDIATE EXECUTION | TRYPSIN PROCESSING |
| | | SCRAPER PROCESSING |
| | | . . . |
| | EXECUTION AFTER PREDETERMINED TIME | AFTER THREE HOURS |
| | | AFTER SIX HOURS |
| | | AFTER 24 HOURS |
| | | . . . |
| CLEANING | IMMEDIATE EXECUTION | . . . |
| | EXECUTION UPON NEXT EXCHANGE OF CULTURE MEDIUM | . . . |
| | EXECUTION UPON NEXT SUBCULTURING | . . . |
| . . . | . . . | . . . |

FIG. 9

CULTURING ASSISTANCE DEVICE, OBSERVATION DEVICE AND PROGRAM

CROSS-REFERENCE TO RELATED APPLICATION

Priority is claimed on Japanese Patent Application No. 2017-015376, filed Jan. 31, 2017, the content of which is incorporated herein by reference. The present application is a continuation application of International Application PCT/JP2017/040066, filed on Nov. 7, 2017. The contents of the above applications are incorporated herein.

BACKGROUND

Technical Field

The present invention relates to a culturing assistance device, an observation device, and a program.

In general, a technology for evaluating cell culture states is a basic technology in a wide range of fields including advanced medicals field such as regenerative medicine or the like, or screening of drugs. For example, in the regenerative medicine field, there are processes of proliferating and differentiating cells in vitro. Furthermore, in the above-mentioned process, it is required to accurately evaluate cell culture states such as the success or failure of differentiation of cells, the existence of canceration or infection of the cells, or the like. As an example, a method of determining cell culture states by performing image processing on an image in which the cells has been captured has been disclosed (see Japanese Unexamined Patent Application, First Publication No. 2004-229619).

SUMMARY

An aspect of the present invention is a culturing assistance device including: an image acquisition unit configured to acquire a captured image of cells during culturing at predetermined timing; a storage control unit configured to store the captured images acquired by the image acquisition unit and event information indicating an event related to culturing of the cells; and a learning unit configured to learn a relationship between the stored captured image and the stored event information.

An aspect of the present invention is an observation device including: a thermostatic chamber configured to maintain an inside thereof in a predetermined environmental conditions while accommodating a culturing container configured to culture cells; an imaging device configured to image the cells contained in the culturing container in the thermostatic chamber at predetermined timing; and the above-mentioned culturing assistance device.

An aspect of the present invention is a program executed in a computer and includes: an image acquisition step of acquiring a captured image of cells during culturing at predetermined timing; a storage control step of storing the captured image acquired in the image acquisition step and event information indicating an event related to the culturing of the cells; and a learning step of learning a relationship between the stored captured image and the stored event information.

DESCRIPTION OF THE EMBODIMENTS

Embodiment

Figure 1:
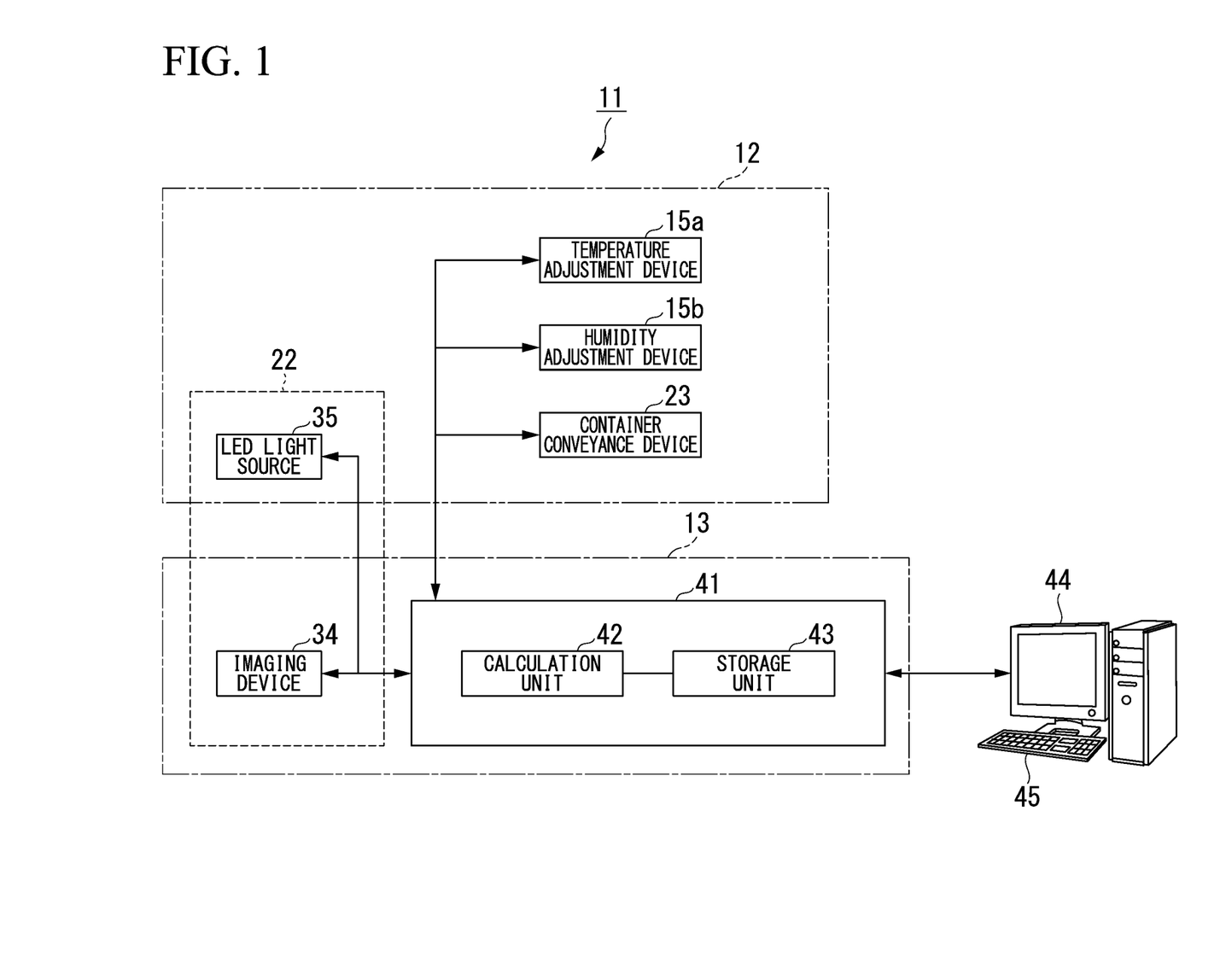
FIG. 1 is a block diagram showing a schematic configuration of an incubator including a culturing assistance device according to an embodiment.
Figure 2:
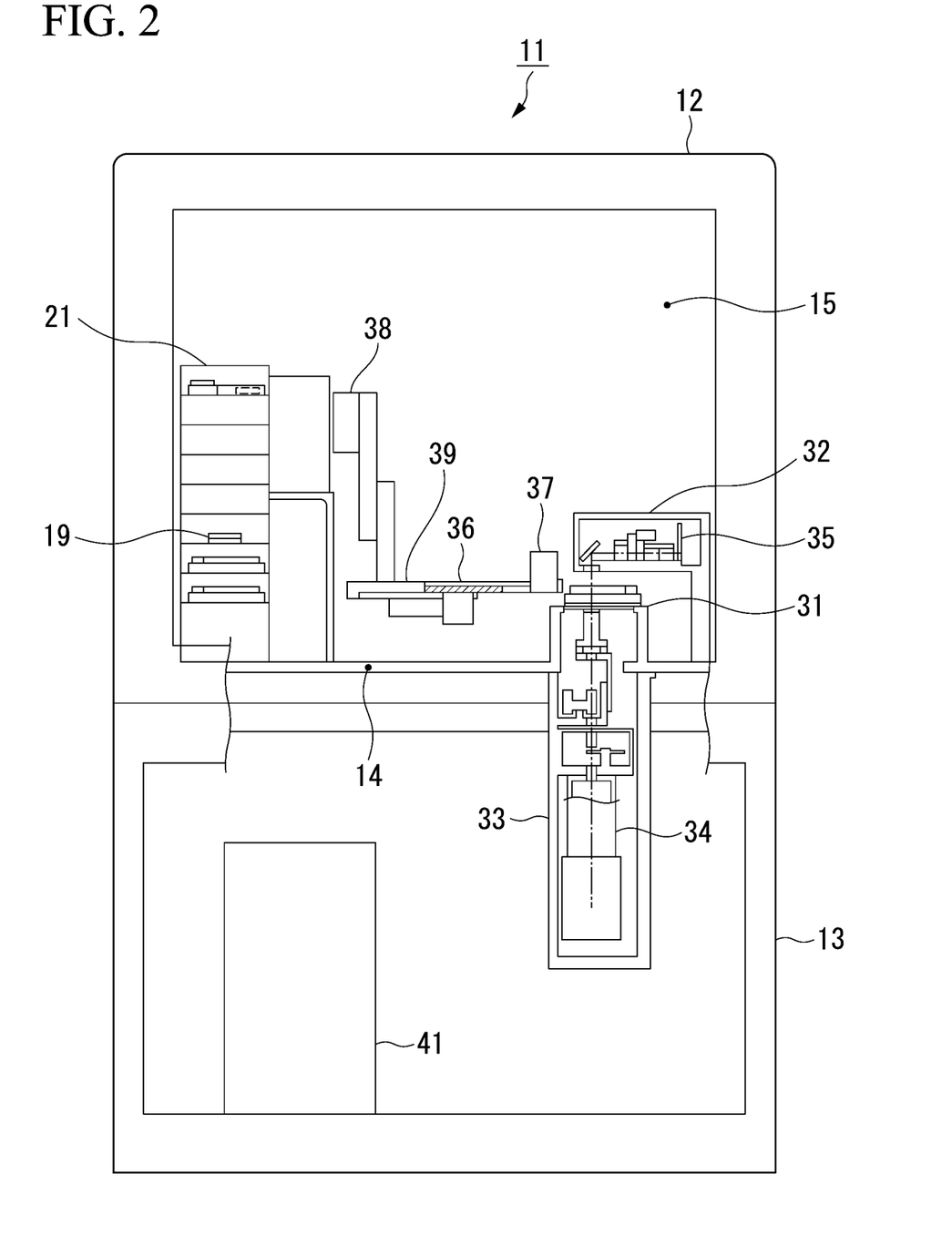
FIG. 2 is a front view of the incubator according to the embodiment.
Figure 3:
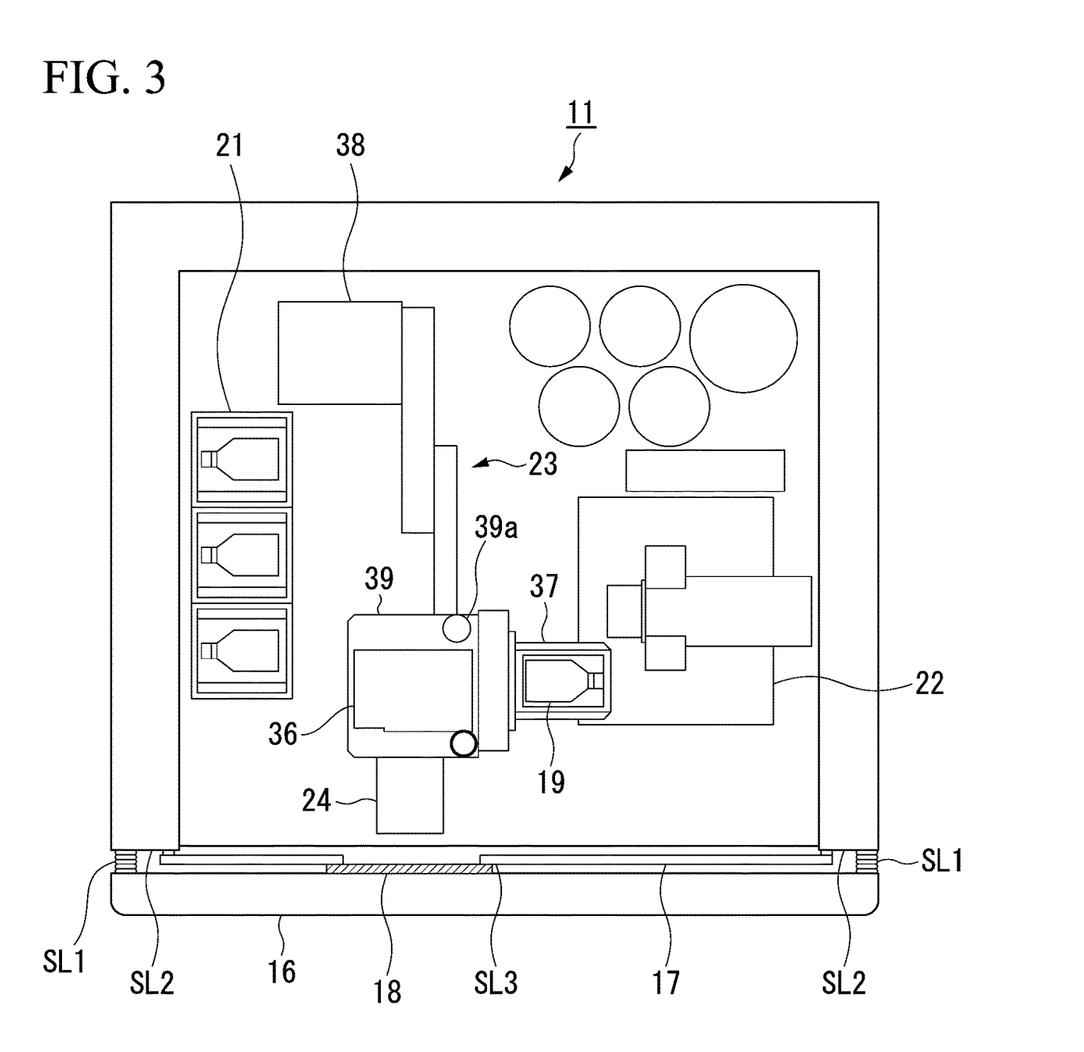
FIG. 3 is a plan view of the incubator according to the embodiment.

Hereinafter, an embodiment of the present invention will be described with reference to the accompanying drawings. FIG. 1 is a block diagram showing a schematic configuration of an incubator 11 including a culturing assistance device according to the embodiment. In addition, FIG. 2 and FIG. 3 are a front view and a plan view of the incubator 11 according to the embodiment.

The incubator 11 is an example of an observation device.

The incubator 11 of the embodiment has an upper casing 12 and a lower casing 13. In an assembled state of the incubator 11, the upper casing 12 is placed above the lower casing 13. Further, internal spaces of the upper casing 12 and the lower casing 13 are partitioned to an upper side and a lower side by a base plate 14.

First, a schematic configuration of the upper casing 12 will be described. A thermostatic chamber 15 configured to perform culturing of cells is formed in the upper casing 12. The thermostatic chamber 15 has a temperature adjustment device 15*a* and a humidity adjustment device 15*b*, and the inside of the thermostatic chamber 15 is maintained at an environment appropriate for culturing of cells (for example, the atmosphere at a temperature of 37° C. and a humidity of 90%) (further, illustration of the temperature adjustment device 15*a* and the humidity adjustment device 15*b* in FIG. 2 and FIG. 3 is omitted).

A large door 16, a middle door 17 and a small door 18 are disposed on a front surface of the thermostatic chamber 15. The large door 16 covers front surfaces of the upper casing 12 and the lower casing 13. The middle door 17 covers the front surface of the upper casing 12 and isolates an environment between the thermostatic chamber 15 and the outside when the large door 16 is open. The small door 18 is a door configured to load and unload a culturing container 19 in which cells are cultured, and is attached to the middle door 17. A variation in environment of the thermostatic chamber 15 can be minimized by loading and unloading the culturing container 19 to/from the small door 18. Further, airtightness of the large door 16, the middle door 17 and the small door 18 is maintained by a packing SL1, a packing SL2 and a packing SL3, respectively.

For operations in which these doors are opened, "exchange of a culture medium," "subculturing," "cleaning," and so on, may be exemplified. Types of these works are selected according to a culturing state of cells. In the following description, these works are also generally referred to as "events." Further, the "events" include an operation performed while the door is not open, no work, stoppage of culturing of cells, or the like.

Further, "exchange of a culture medium" is to exchange the whole or some of a culture medium in a culturing container with a new culture medium. In addition, "subculturing" is to collect bred cells and replate them in a separate culturing container. In addition, "cleaning" is to clean the inside of the incubator. The cleaning includes sterilization of an incubator surface, disinfection of water required for maintaining the humidity in the incubator, or the like.

In addition, a stocker 21, an observation unit 22, a container conveyance apparatus 23 and a conveyance base 24 are disposed in the thermostatic chamber 15. Here, the conveyance base 24 is disposed in front of the small door 18, and loads and unloads the culturing container 19 to/from the small door 18.

The stocker 21 is disposed on a left side of the thermostatic chamber 15 when seen from a front surface (a lower side of FIG. 3) of the upper casing 12. The stocker 21 has a plurality of shelves, and the plurality of culturing containers 19 can be received in each of the shelves of the stocker 21. Further, cells that are objects of culturing are accommodated in each of the culturing containers 19 together with a culture medium.

The observation unit 22 is disposed on a right side of the thermostatic chamber 15 when seen from the front surface of the upper casing 12. The observation unit 22 can execute time lapse observation of the cells in the culturing container 19. Here, the time lapse observation is a technique of observing time-series variation of a sample by imaging the same at predetermined timings on the basis of an imaging schedule that is previously set. Imaging of the sample may be performed at a constant time interval or may be performed at differing time intervals.

Here, the observation unit 22 is disposed to be fitted into an opening section of the base plate 14 of the upper casing 12. The observation unit 22 has a specimen support 31, a stand arm 32 overhanging upward from the specimen support 31, a microscopic optical system for phase difference observation, and a main body portion 33 in which an imaging device 34 is installed. Further, the specimen support 31 and the stand arm 32 are disposed in the thermostatic chamber 15, and the main body portion 33 is disposed in the lower casing 13.

The specimen support 31 is formed of a material having transmittance, and the culturing container 19 can be placed thereon. The specimen support 31 is configured to be movable in a horizontal direction, and can adjust a position of the culturing container 19 placed on an upper surface thereof. In addition, an LED light source 35 is installed in the stand arm 32. Further, the imaging device 34 can acquire a microscopic image of cells by imaging the cells in the culturing container 19, that has been transmission-illuminated from above the specimen support 31 using the stand arm 32, via a microscopic optical system.

The container conveyance apparatus 23 is disposed at a center of the thermostatic chamber 15 when seen from the front surface of the upper casing 12. The container conveyance apparatus 23 performs delivery of the culturing container 19 between the stocker 21, the specimen support 31 of the observation unit 22 and the conveyance base 24.

As shown in FIG. 3, the container conveyance apparatus 23 has a vertical robot 38 having an articulated arm, a rotating stage 39, a mini-stage 36 and an arm section 37. The rotating stage 39 is attached to a tip portion of the vertical robot 38 via a rotary shaft 39a to be rotatable by 180° in the horizontal direction. For this reason, the rotating stage 39 can cause the arm section 37 to face the stocker 21, the specimen support 31 and the conveyance base 24.

In addition, the mini-stage 36 is attached to the rotating stage 39 to be slidable in the horizontal direction. The arm section 37 configured to grip the culturing container 19 is attached to the mini-stage 36.

Next, a schematic configuration of the lower casing 13 will be described. The main body portion 33 of the observation unit 22 or a control device 41 of the incubator 11 is accommodated in the lower casing 13.

The control device 41 is connected to the temperature adjustment device 15a, the humidity adjustment device 15b, the observation unit 22 and the container conveyance apparatus 23. The control device 41 includes a calculation unit 42 and a storage unit 43, and generally controls respective parts of the incubator 11 according to a predetermined program. The control device 41 is an example of the culturing assistance device.

As an example, the control device 41 controls the temperature adjustment device 15a and the humidity adjustment device 15b such that predetermined environmental conditions are maintained inside the thermostatic chamber 15. In addition, the control device 41 controls the observation unit 22 and the container conveyance apparatus 23 such that an observation sequence of the culturing container 19 is automatically executed on the basis of a predetermined observation schedule. Further, the control device 41 executes culturing state evaluation processing that performs evaluation of a culturing state of cells on the basis of the image acquired through an observation sequence.

[Example of Observing Operation]

Next, an example of an observing operation in the incubator 11 will be described with reference to a flowchart in FIG. 4.

Figure 4:
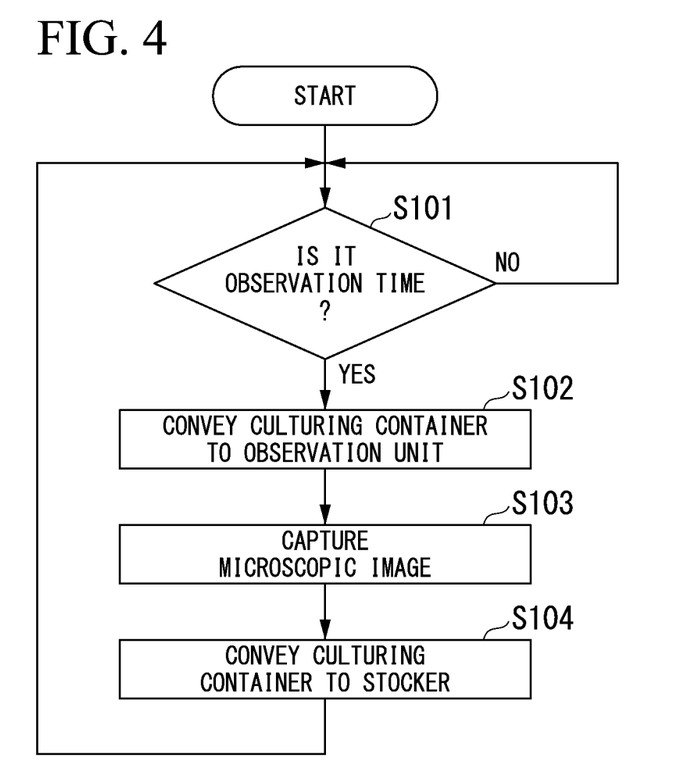
FIG. 4 is a view showing an example of an observing operation in the incubator according to the embodiment.

FIG. 4 is a view showing an example of the observing operation in the incubator 11 of the embodiment. FIG. 4 shows an operation example in which time lapse observation of the culturing container 19 loaded into the thermostatic chamber 15 is performed according to a registered observation schedule.

(Step S101)

The calculation unit 42 compares an observation schedule of management data of the storage unit 43 with the current date and time, and determines whether an observation starting time of the culturing container 19 has reached the current date and time. When the observation starting time has reached the current date and time (a YES side), the calculation unit 42 moves to processing in S102. Meanwhile, when it is not an observation time of the culturing container 19 (a NO side), the calculation unit 42 stands by until a time of the next observation schedule.

(Step S102)

The calculation unit 42 instructs conveyance of the culturing container 19 corresponding to the observation schedule to the container conveyance apparatus 23. Then, the container conveyance apparatus 23 unloads the instructed culturing container 19 from the stocker 21 and places the unloaded culturing container 19 on the specimen support 31 of the observation unit 22. Further, in a step in which the culturing container 19 is placed on the specimen support 31, the entire observation image of the culturing container 19 is captured by a bird view camera (not shown) installed in the stand arm 32.

(Step S103)

The calculation unit 42 instructs imaging of a microscopic image of cells to the observation unit 22. The observation unit 22 drives the imaging device 34 and captures a microscopic image of cells in the culturing container 19 while turning on the LED light source 35 and illuminating the culturing container 19.

Here, the imaging device 34 captures a microscopic image on the basis of imaging conditions (a magnification of an objective lens, an observation point in a container) designated by a user on the basis of management data stored in the storage unit 43. For example, when a plurality of points in the culturing container 19 are observed, the observation unit 22 adjusts positions of the culturing containers 19 according to driving of the specimen support 31 in sequence, and captures microscopic images of each of the points. Further, data of the microscopic images acquired in S103 is read by the control device 41, and recorded on the storage unit 43 under control of the calculation unit 42.

(Step S104)

The calculation unit 42 instructs conveyance of the culturing container 19 to the container conveyance apparatus 23 after completion of the observation schedule. Then, the container conveyance apparatus 23 conveys the instructed culturing container 19 from the specimen support 31 of the observation unit 22 to a predetermined receiving position of the stocker 21. After that, the calculation unit 42 terminates the observation sequence and returns to processing in S101.

According to the above-mentioned sequence, the time-series image data observed by the incubator 11 is stored in the storage unit 43. In the following description, obtaining the time-series image data using the incubator 11 is also referred to as time lapse imaging.

[Function of Associating Image Captured by Time Lapse and Event]

Next, a function of an associating image and an event will be described with reference to FIG. 5 to FIG. 9.

Figure 5:
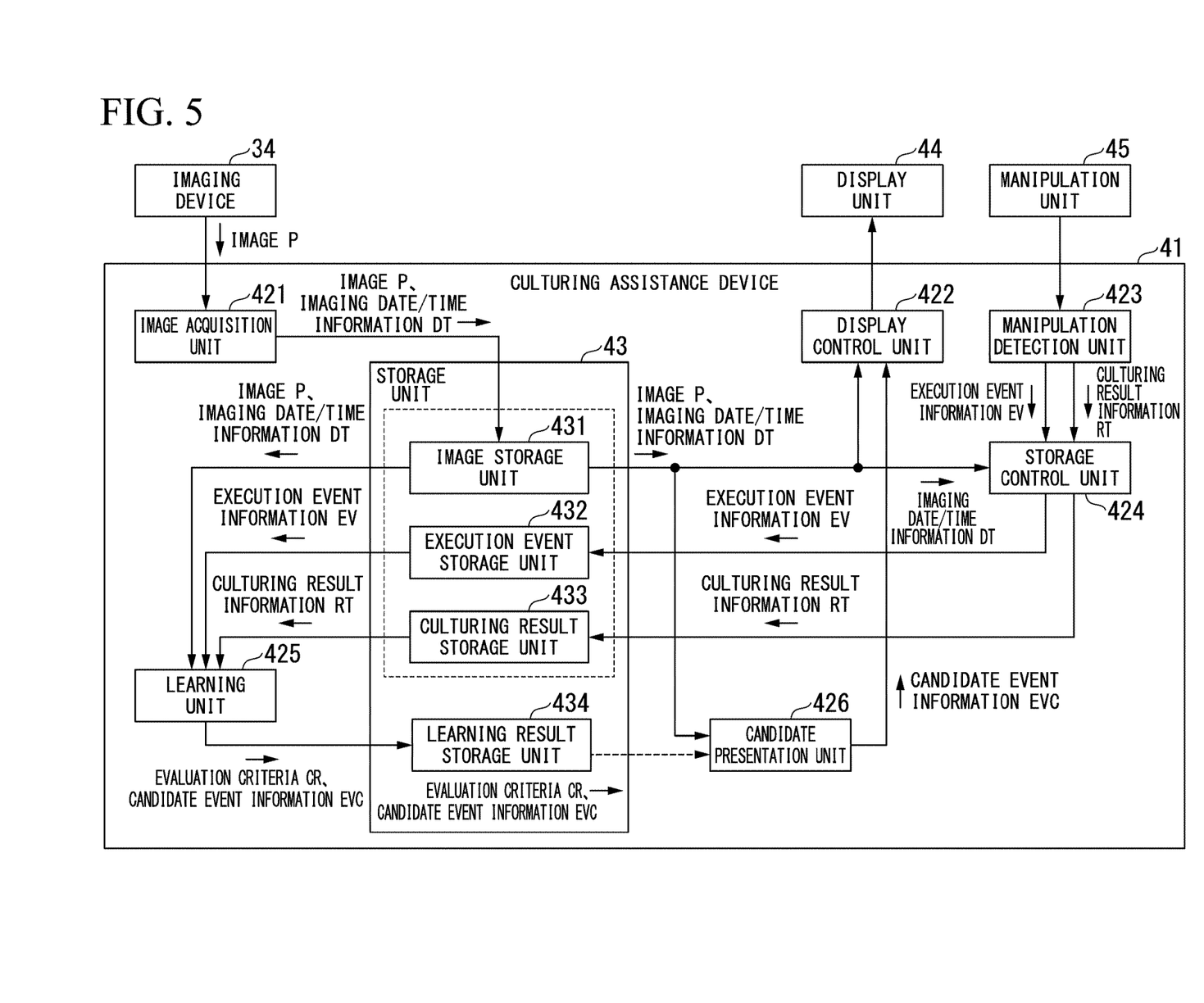
FIG. 5 is a view showing an example of a functional configuration of a control device according to the embodiment.

FIG. 5 is a view showing an example of a functional configuration of the control device 41 of the embodiment. As described above, the control device 41 includes the calculation unit 42 and the storage unit 43.

The calculation unit 42 includes an image acquisition unit 421, a display control unit 422, a manipulation detection unit 423, a storage control unit 424 and a learning unit 425 as function units thereof.

The storage unit 43 includes an image storage unit 431, an execution event storage unit 432, a culturing result storage unit 433 and a learning result storage unit 434.

The image acquisition unit 421 acquires an image P from the imaging device 34. The image P is an image of cells during culturing captured at, for example, predetermined timings on the basis of the imaging schedule.

The image acquisition unit 421 adds imaging date and time information DT showing an imaging date and time and stores the imaging date and time information DT in the image storage unit 431 when the image P is acquired from the imaging device 34.

Figure 6:
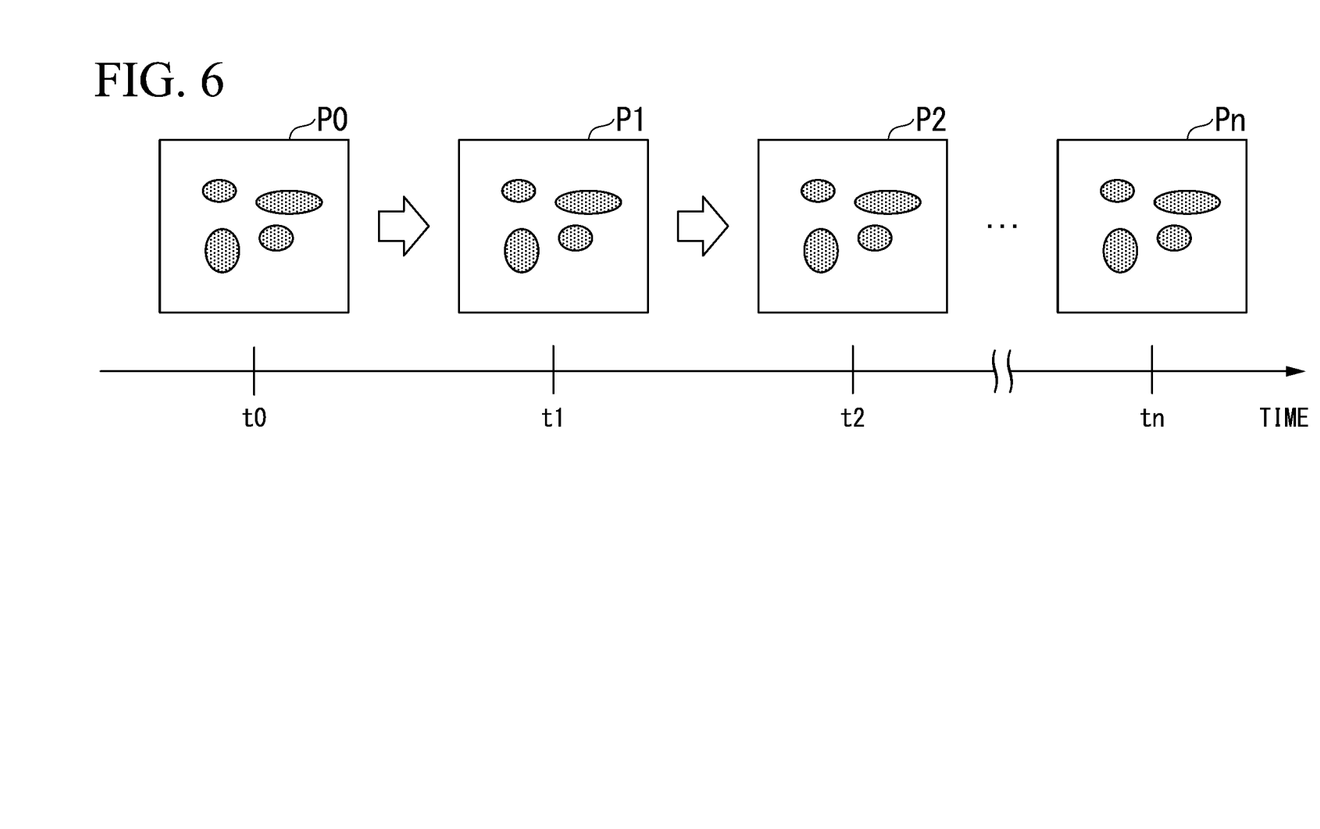
FIG. 6 is a view showing an example of an image stored in an image storage unit according to the embodiment.

FIG. 6 is a view showing an example of the image P stored in the image storage unit 431 of the embodiment. In the example, the imaging device 34 captures an image at each of times of time t0, time t1, time t2 . . . time tn. For example, the image P0 is an image captured at the time t0. The image acquisition unit 421 stores the image P0 in the image storage unit 431 together with the imaging date and time information DT showing the time t0 when the image P0 is acquired from the imaging device 34 at the time t0. Also in the image P1 to the image Pn, the image acquisition unit 421 stores each of the image P in the image storage unit 431 together with the imaging date and time information DT.

Returning to FIG. 5, the display control unit 422 controls screen display of a display unit 44. Specifically, the display control unit 422 displays the image P stored in the image storage unit 431 and event candidates related to the image P on the display unit 44. An example of the screen displayed on the display unit 44 will be described with reference to FIG. 7.

Figure 7:
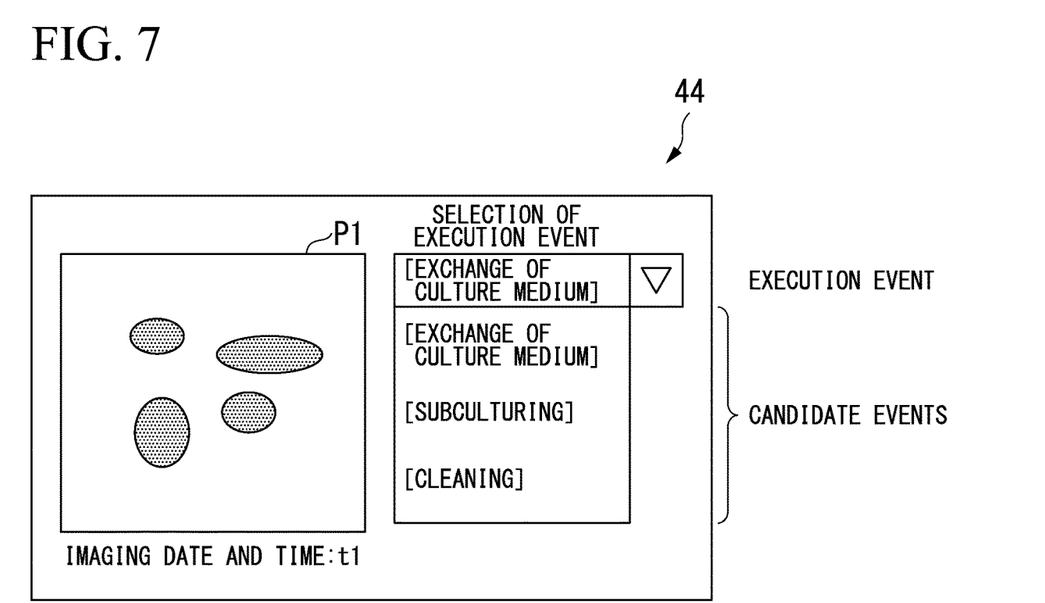
FIG. 7 is a view showing an example of a screen displayed on a display unit according to the embodiment.

FIG. 7 is a view showing an example of a screen displayed on the display unit 44 of the embodiment. The image P and the event candidates related to the image P are displayed on the display unit 44. In the example, "the image P1 at the time t1" serving as the image P is displayed on the display unit 44. In addition, "exchange of a culture medium," "subculturing" and "cleaning" serving as event candidates related to the image P1 are displayed on the display unit 44.

In a case the observer, who has seen the image P1 displayed on the display unit 44, determines that it is time to perform the "exchange of a culture medium" based on the state of the image P, the incubator 11 is extracted from the culturing container 19 and an operation of exchanging the culture medium is performed. In this case, the observer selects the "exchange of a culture medium" as an execution event. Selection of the execution event may be before the event is performed actually or may be after the event is actually performed. Further, the selected event is not limited to one and may be two or more.

A manipulation unit 45 includes a touch panel, a mouse, a keyboard, or the like. The observer selects an execution event by manipulating the manipulation unit 45. In the above-mentioned example, when exchange of a culture medium is performed, the observer manipulates the manipulation unit 45 and selects the "exchange of a culture medium" as the execution event.

Further, in the above-mentioned example, while an aspect in which the selected event is previously stored has been described, there is no limitation thereto. When the event to be executed is not included in the displayed event candidates, the observer may add a new event candidates using the manipulation unit 45 or the like.

In addition, when there is an unnecessary event in the displayed event candidates, the observer may delete the unnecessary event from the candidates using the manipulation unit 45 or the like.

The manipulation detection unit 423 detects a manipulation with respect to the manipulation unit 45. The manipulation detection unit 423 generates event information EV according to the manipulation when the manipulation is detected. In the above-mentioned example, when the observer performs a manipulation of selecting "exchange of a culture medium" with respect to the manipulation unit 45, the manipulation detection unit 423 detects that the "exchange of a culture medium" is selected as the execution event. The manipulation detection unit 423 generates the event information EV showing the "exchange of a culture medium."

The storage control unit 424 controls writing of information with respect to the storage unit 43. Specifically, the storage control unit 424 stores the image acquired by the image acquisition unit 421 and the event information EV showing the event related to culturing of cells at a timing when the image was captured in the execution event storage unit 432 while associating the image acquired by the image acquisition unit 421 and the event information EV with each other.

In the above-mentioned example, a specific example of the information stored in the execution event storage unit 432 will be described. The image P is displayed on the display unit 44. The image P1 is an image captured at the time t1. In this case, "the timing when the image P1 was captured" is the time t1. The image P1 has the imaging date and time information DT that indicates the time t1.

When the observer sees the image P1 and selects the "exchange of a culture medium" from the event candidates, the manipulation detection unit 423 generates the event information EV showing the "exchange of a culture medium." In this case, the event related to the culturing of the cells at the timing when the image was captured, i.e., the time t1, is the "exchange of a culture medium." That is, the manipulation detection unit 423 generates the event information EV that indicates "exchange of a culture medium" as the event related to the culturing of the cells at the timing when the image was captured.

The storage control unit 424 stores the imaging date and time information DT shown in the image P1 in the execution event storage unit 432 together with the event information EV generated by the manipulation detection unit 423.

In addition, the storage control unit 424 may additionally store the information related to the date and time when the event is executed with respect to the event information EV. In this case, the event information EV includes the information related to the date and time when the event is executed.

That is, the storage control unit 424 correspondingly stores the image acquired by the image acquisition unit 421 and the event information EV that indicates the event related to the culturing of the cells at the timing when the image was captured.

Further, when "no work" is selected as the event, the storage control unit 424 may store the event information that indicates "no work" while associated with the image, or may not store the event information that indicates "no work" by assuming that none of a specific event was selected.

Further, as described above, while the example in which the image acquisition unit 421 adds the imaging date and time information DT to the image P has been described, there is no limitation thereto. The storage control unit 424 may add the imaging date and time information DT to the image P. That is, the storage control unit 424 may further store the information related to the date and time when the image P was captured. In addition, the storage control unit 424 may correspondingly store the imaging date and time information DT and the event information EV when the imaging date and time information DT is stored.

The learning unit 425 learns a relationship between the image stored in the image storage unit 431 and the event information EV corresponding to the image. The learning unit 425 learns a relationship between these pieces of information using various known techniques.

In the above-mentioned example, the learning unit 425 learns a relationship between the image P1 and the event information EV that indicates "exchange of a culture medium." For example, the learning unit 425 learns that the "exchange of a culture medium" is performed in a state of the cells shown in the image P1. That is, the learning unit 425 learns the states of the cells in which the "exchange of a culture medium" is performed. The learning result is stored in the learning result storage unit 434. The learning unit 425 obtains, for example, whether execution of "exchange of a culture medium" in a state of the image P1 was appropriate, whether a timing of "exchange of a culture medium" was appropriate, or the like, as learning results according to accumulation of the learning. Here, the learning unit 425 may execute learning in consideration of a variation between a state of the cells in the image P0 captured at the time t0 and a state of the cells in the image P1 captured at the time t1. That is, the learning may be performed using the image captured at the time before the time when the image P1 was captured. In addition, there is no limitation thereto, and the learning may also be performed in consideration of a variation between the state of the cells in the image P2 captured at the time t2 and the state of the cells in the image P1 captured at the time t1. That is, the learning may be performed using the image captured at the time after the time when the image P1 was captured. Accuracy of the learning results can be improved by executing the learning using images obtained in time series. The learning unit 425 stores the obtained learning results in the learning result storage unit 434.

Event candidates to be performed in the state of the cells shown in the image P1 are obtained as the learning results by the learning unit 425. In this case, the learning unit 425 generates candidate event information EVC showing event candidates to be performed. The learning unit 425 stores the generated candidate event information EVC in the learning result storage unit 434.

For example, the learning unit 425 learns "exchange of a culture medium," "subculturing" or "cleaning" as event candidates to be executed in the state of the cells shown in the image P1.

Further, the learning unit 425 may execute the learning using deep learning. The deep learning is mechanical learning executed in a neural network having an input layer, an intermediate layer, and an output layer (a deep neural network), in which the intermediate layer is provided as multiple layers. When the deep learning is used, a feature quantity that cannot be recognized through observation by a human may also be extracted, and the state of the cells during culturing is appropriately evaluated.

A candidate presentation unit 426 presents "a candidate event" shown in FIG. 7. The candidate presentation unit 426 may present the candidate event on the basis of the results learned by the learning unit 425, or may present the candidate event without relying on the results learned by the learning unit 425. First, the case in which the candidate presentation unit 426 presents the candidate event without relying on the results learned by the learning unit 425 will be described. Further, while the presentation will be described as display on the display unit 44 as shown in FIG. 7, there is no limitation thereto, and for example, the presentation may be output to another device.

[Case in which Candidate Event is Presented without Relying on Learning Results]

The candidate presentation unit 426 acquires "a candidate event" from the storage unit 43. Here, an example of the candidate event information EVC stored in the storage unit 43 will be described with reference to FIG. 8.

Figure 8:
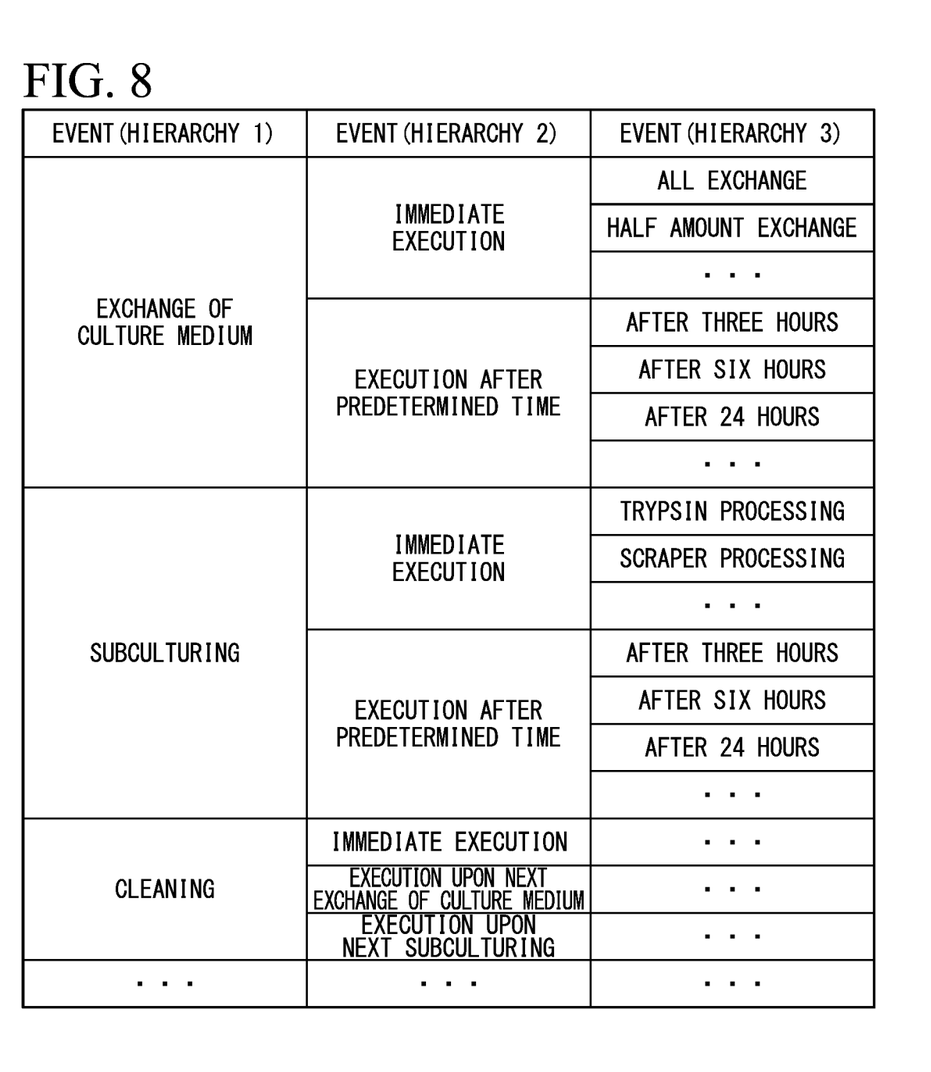
FIG. 8 is a view showing an example of candidate event information according to the embodiment.

FIG. 8 is a view showing an example of the candidate event information EVC of the embodiment. In the candidate event information EVC, events are hierarchically divided. In the example, the events are hierarchically divided into three hierarchies.

As the example shown in FIG. 8, "exchange of a culture medium," "subculturing" and "cleaning" are provided in an event (a hierarchy 1). "Immediate execution," "execution after a predetermined time" . . . are provided in an event (a hierarchy 2) of the "exchange of a culture medium." Further, while not shown, information of an observer who performs the events may be displayed as event information.

The candidate presentation unit 426 outputs the acquired candidate event information EVC to the display control unit 422. As a result, as shown in FIG. 7, "exchange of a culture medium," "subculturing" or "cleaning" in a state of the cells shown in the image P1 is displayed as a candidate event on the display unit 44.

[Case in which Candidate Event is Presented on the Basis of Learning Results]

The candidate presentation unit 426 acquires the image P displayed on the display unit 44 by the display control unit 422. In the example shown in FIG. 7, the display control unit 422 displays the image P1 on the display unit 44. In this case, the candidate presentation unit 426 acquires the image P1.

The candidate presentation unit 426 matches the acquired image P1 with the candidate event information EVC stored in the learning result storage unit 434 using a known technique. The candidate presentation unit 426 acquires the candidate event information EVC matched with the image P1 from the learning result storage unit 434. The candidate event information EVC is some of the learning results by the learning unit 425. In the above-mentioned example, the learning unit 425 learns "exchange of a culture medium," "subculturing" or "cleaning" as event candidates to be executed in the state of the cells shown in the image P1. The candidate presentation unit 426 acquires "exchange of a culture medium," "subculturing" or "cleaning" as the candidate event information EVC corresponding to the image P1.

That is, the candidate presentation unit 426 presents the candidates for the executed event on the basis of the learning results by the learning unit 425 and the image acquired by the image acquisition unit 421. For example, the candidate presentation unit 426 presents the event candidates to be executed at the timing when the image acquired by the image acquisition unit 421 is captured, among the plurality of event candidates.

Further, the candidate presentation unit 426 may present the candidates for the executed event on the basis of a newest image among the plurality of images P stored in the image storage unit 431. In this case, the plurality of images P having different imaging dates and times and captured at predetermined timings are stored in the image storage unit 431. The image acquisition unit 421 acquires the newest image among the plurality of images P stored in the image storage unit 431. The candidate presentation unit 426 presents the event candidates to be executed on the basis of the learning results by the learning unit 425 and the newest image acquired by the image acquisition unit 421.

These candidate event information EVC function as a guide when an observer selects the execution event in the case in which the image P is displayed on the display unit 44. Since the candidate event is displayed on the display unit 44, which kind of event should be performed is shown to an observer in the case in which a cell is in the state as shown in the image P. That is, the control device 41 functions as an assistance device of cell culturing. The control device 41 can assist the cell culturing by reducing labor and time of event recording of an observer when the cells are cultured.

[Variant (1)]

The learning unit 425 may execute learning of the culturing results in addition to learning of a culturing progress of the cells. In this case, the learning unit 425 learns a relationship between culturing result information RT, the image P and the event information EV. The variant will be described with reference to FIG. 9.

Figure 9:
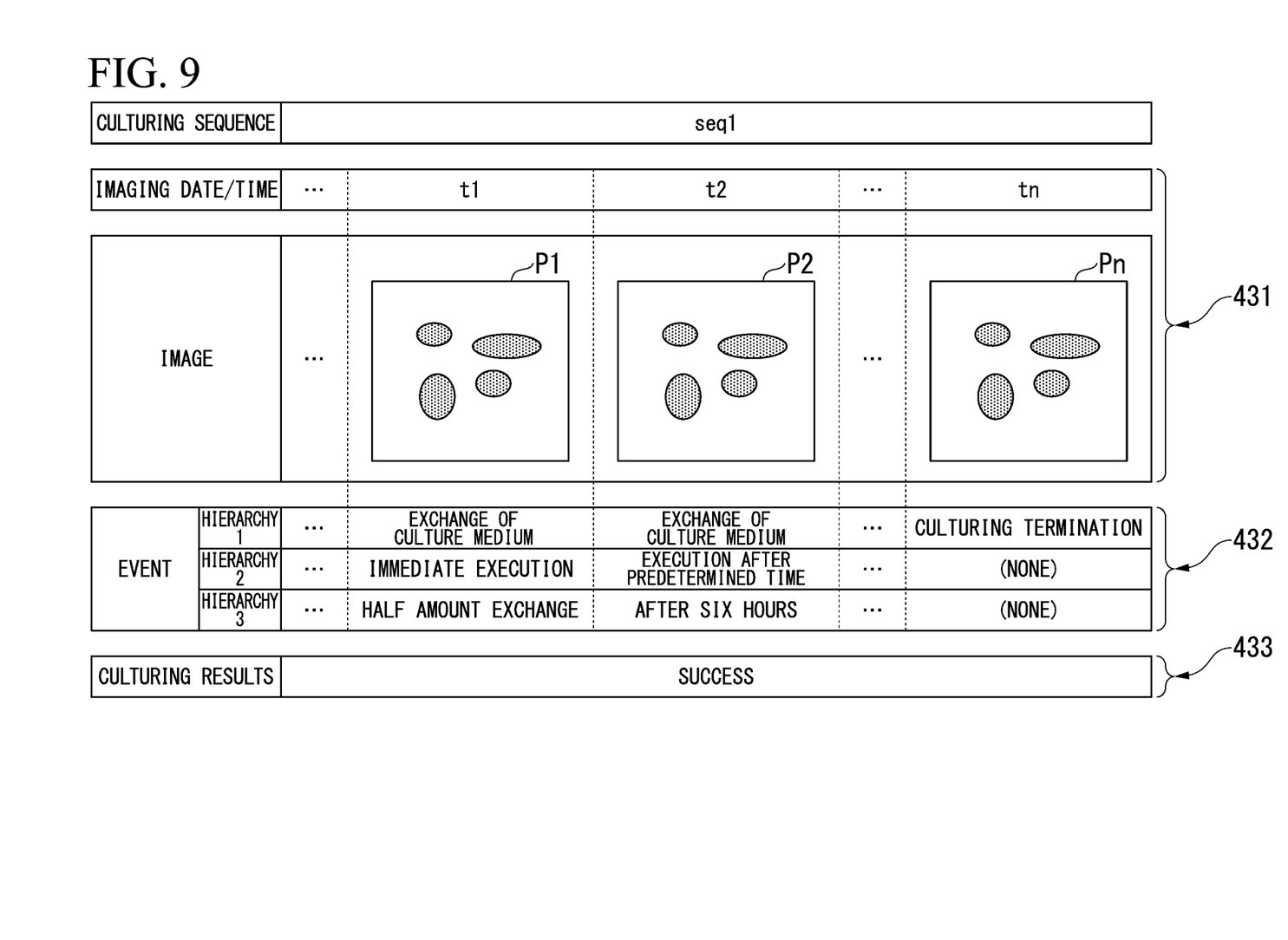
FIG. 9 is an example of information stored in a storage unit according to the embodiment.

FIG. 9 shows an example of information stored in the storage unit 43 of the embodiment. In the example shown in FIG. 9, a culturing progress and culturing results in a culturing sequence seq1 are stored in the storage unit 43. In the culturing sequence seq1, the images P are captured at time t1, time t2 . . . time t3. As described above, these images P correspond to the imaging date and time information DT and are stored in the image storage unit 431 in time series.

In addition, the event information EV is correspondingly provided in each of the images P. In the example, "exchange of a culture medium," "immediate execution" and "half amount exchange" correspond to the images P1 as the event information EV. As described above, these pieces of event information EV are stored in the execution event storage unit 432.

When culturing sequence seq1 is terminated, information indicating whether culturing has succeeded or failed is stored in the culturing result storage unit 433 as the culturing result information RT.

What kind of state is success or failure, i.e., the culturing result is determined according to a culturing purpose of the cells. An example of a relation between the culturing purpose of the cells and the culturing result will be described.

(1) Case of Culturing for Increasing Number of Cells

Cultivation for increasing the number of cells that are a certain type is provided. In this case, it is determined as success when the number of the cells upon completion of the culturing sequence exceeds a predetermined threshold value.

(2) Case of Culturing for Differentiation Induction

Cultivation for differentiation from the certain type cells to desired type cells is provided. In this case, it is determined as success when a ratio of the number of the desired type cells with respect to the number of all of the cells upon completion of the culturing sequence exceeds a predetermined threshold value.

When the culturing has succeeded or failed, the observer manipulates the manipulation unit 45, and performs manipulation showing the culturing result. The manipulation detection unit 423 generates the culturing result information RT by detecting the manipulation.

The storage control unit 424 stores the culturing result information RT generated by the manipulation detection unit 423 in the culturing result storage unit 433. A state of the culturing result storage unit 433 when the culturing result in the culturing sequence seq1 is success is shown in FIG. 9.

The learning unit 425 learns a relationship between the culturing result information RT, the image P and the event information EV stored in the storage control unit 424.

According to the above-mentioned configuration, the learning unit 425 can make not only the culturing progress become a learning object but also can make the culturing result become a learning object. For example, the learning unit 425 learns the event stored in the execution event storage unit 432 as "an appropriate work" for making success of culturing when the culturing has succeeded, and learns the event as "an inappropriate work" when the culturing has failed. In addition, the learning unit 425 leans a time when the event is executed as "an inappropriate time." Accordingly, the candidate presentation unit 426 can present an appropriate event for making a success of culturing as a candidate event. In addition, the candidate presentation unit 426 can present an appropriate time when the candidate event is executed. For example, when "execution after a predetermined time (after three hours)" related to the exchange of a culture medium is learned as inappropriate, "execution after a predetermined time (after six hours)" may be presented as an appropriate event.

Further, when a success rate of the cell culturing is expected to be low, discontinuation of the culturing of the cells can also be presented as a candidate event. When the culturing of the cells is discontinued at a relatively initial step, unnecessary costs applied to the culturing can be reduced.

[Variant (2)]

When there is more than one candidate event, the candidate presentation unit 426 may present a priority order to be executed to each of the candidate events. In this case, the learning unit 425 ranks the candidate events on the basis of the culturing progress or the culturing results. The learning unit 425 stores the ranked results as an evaluation criteria CR while being associated with the candidate event information EVC to the learning result storage unit. The priority order is applied to each of the candidate events according to, for example, a success rate of the cell culturing, a proliferating speed of the cells, or the like.

The candidate presentation unit 426 ranks a plurality of candidates on the basis of the evaluation criteria CR associated with the candidate event when the plurality of candidate events are stored in the learning result storage unit 434.

According to the above-mentioned configuration, the candidate events are ranked and displayed on the display unit 44. That is, the control device 41 can perform assistance of the cell culturing by reducing labor and time of event selection of an observer when the cells are cultured. Further, all of the plurality of candidate events may not be provided, and for example, a configuration in which only candidate events of a predetermined success rate or more are presented and candidate events less than a predetermined success rate are not presented may be provided. In addition, for example, a configuration in which only a success rate of the culturing is presented with no priority may be provided.

Further, a program for executing various types of processing of the observation device 1 or the culturing assistance device 41 according to the embodiment of the present invention may be recorded on a computer-readable recording medium, the program recorded on the recording medium may be read and executed by a computer system, and the above-mentioned various types of processing may be performed.

Further, the "computer system" disclosed herein may include OD or hardware such as peripheral devices or the like. In addition, the "computer system" also includes a homepage providing environment (or a display environment) when a WWW system is used. In addition, the "computer-readable recording medium" refers to a writable non-volatile memory such as a flexible disk, a magneto-optic disk, a ROM, a flash memory, or the like, a portable medium such as a CD-ROM or the like, and a storage device such as a hard disk or the like installed in the computer system.

Further, the "computer-readable recording medium" is configured to hold a program for a constant time like a volatile memory (for example, a dynamic random access memory (DRAM) in the computer system that is a server or a client when the program is transmitted via a network such as the Internet or the like or a communication line such as a telephone line or the like. In addition, the program may be transmitted to another computer system from the computer system, in which the program is stored in a storage device or the like, via a transmissive medium or by a transmission wave in the transmission medium. Here, the "transmission medium" through which the program is transmitted is referred to as a medium having a function of transmitting information, for example, a network (a communication line) such as the Internet or the like or a communication line (a communication wire) such as a telephone line or the like. In addition, the program may be configured to realize some of the above-mentioned functions. Further, a so-called differential file (a differential program) in which the above-mentioned functions can be realized in combination with a program already recorded on a computer system may be provided.

Hereinabove, while the embodiment of the present invention has been described in detail with reference to the accompanying drawings, a specific configuration is not limited to the embodiment and also includes designs without departing from the scope of the present invention.

What is claimed is:

1. A culturing assistance device comprising:
a processor;
a memory encoded with instructions executed by the processor, the instructions causing the processor to perform operations comprising:
acquiring a captured image of cells at every predetermined time during a cell culturing process of the cells;
storing the captured image and event information indicating an event related to culturing of the cells at the timing when the image was captured and culturing result information indicating culturing results of the cells, wherein the event comprises at least one of "exchange of a culture medium configured to culture the cells", "subculturing of the cells" and "cleaning of an inside of a device in which culturing of the cells is performed";
learning a relationship between the stored captured image, the stored event information and the stored culturing result information, wherein the learning learns that the event to be executed in a state of the cells shown in the stored captured image; and
presenting a candidate event candidate to be executed on the basis of the learning results and the acquired image, wherein the candidate event is the stored event information.

2. The culturing assistance device according to claim 1, further comprising storing information related to a date and time when the captured image was captured.

3. The culturing assistance device according to claim 2, further comprising correspondingly storing the information related to the date and time when the captured image was captured and the event information.

4. The culturing assistance device according to claim 1, wherein the event information comprises information related to a date and time when the event is executed.

5. The culturing assistance device according to claim 1, further comprising:
storing culturing result information indicating culturing results of the cells, and
learning a relationship between the culturing result information, the captured image and the stored event information.

6. The culturing assistance device according to claim 1, further comprising presenting event candidates to be executed on the basis of learning results and a newest image acquired.

7. The culturing assistance device according to claim 6, wherein, when a plurality of event candidates to be executed are provided, assigning and presenting a priority order to be executed for the plurality of event candidates on the basis of the learning results.

8. The culturing assistance device according to claim 7, wherein the priority order is applied according to a success rate of cell culturing.

9. The culturing assistance device according to claim 6, further comprising detecting a selection manipulation that selects an event to be executed from the event candidates presented, storing the image and the event information indicated by the selection manipulation detected, and learning a relationship between the image and the event information on the basis of the event information indicated by the selection manipulation.

10. The culturing assistance device according to claim 1, further comprising:

selecting the event among the candidate event, and storing the captured image and the event information indicating the selected event.

11. The culturing assistance device according to claim 1, wherein the learning learns the event as "appropriate work" when the culturing has succeeded, and learns the event as "inappropriate work" when the culturing has failed.

12. The culturing assistance device according to claim 1, further comprising:

presenting an appropriate event for making a success of culturing as a candidate event candidate to be executed on the basis of the learning results and the acquired image, the appropriate event including "stopping the cell culturing".

13. The culturing assistance device according to claim 1, further comprising:

presenting an appropriate time when the candidate event is executed.

14. An incubator comprising:

a thermostatic chamber configured to maintain an inside thereof in a predetermined environmental condition while accommodating a culturing container configured to culture cells;

an imaging device configured to image the cells contained in the culturing container in the thermostatic chamber at every predetermined time during a cell culturing process of the cells;

a processor; and a memory encoded with instructions executed by the processor, the instructions causing the processor to perform operations comprising:

acquiring a captured image of cells during culturing at every predetermined time;

storing the captured image and event information indicating an event related to the culturing of the cells at the timing when the image was captured and culturing result information indicating culturing results of the cells, wherein the event comprises at least one of "exchange of a culture medium configured to culture the cells", "subculturing the of the cells" and "cleaning of an inside of a device in which culturing of the cells is performed";

learning a relationship between the stored captured image, the stored event information and the stored culturing result information, wherein the learning learns that the event to be executed in a state of the cells shown in the stored captured image; and presenting a candidate event candidate to be executed on the basis of the learning results and the acquired image, wherein the candidate event is the stored event information.

15. The incubator according to claim 14, wherein the learning learns the event as "appropriate work" when the culturing has succeeded, and learns the event as "inappropriate work" when the culturing has failed.

16. The incubator according to claim 14, further comprising:

presenting an appropriate event for making a success of culturing as a candidate event candidate to be executed on the basis of the learning results and the acquired image, the appropriate event including "stopping the cell culturing".

17. The incubator according to claim 14, further comprising:

presenting an appropriate time when the candidate event is executed.

18. A non-transitory computer-readable storage medium storing a program which, when executed in a computer, causes the computer to execute processes comprising:

acquiring a captured image of cells during culturing at every predetermined time;

storing the captured image acquired and event information indicating an event related to the culturing of the cells at the timing when the image was captured and culturing result information indicating culturing results of the cells, wherein the event comprises at least one of "exchange of a culture medium configured to culture the cells", "subculturing of the cells" and "cleaning of an inside of a device in which culturing of the cells is performed";

learning a relationship between the stored captured image, the stored event information and the stored culturing result information, wherein the learning learns that the event to be executed in a state of the cells shown in the stored captured image; and presenting a candidate event candidate to be executed on the basis of the learning results and the acquired image, wherein the candidate event is the stored even information.

* * * * *